United States Patent [19]

Sawada et al.

[11] Patent Number: 5,089,262

[45] Date of Patent: Feb. 18, 1992

[54] **E87AG ANTIGENS OF *PSEUDOMONAS AERUGINOSA* AND MONOCLONAL ANTIBODIES AGAINST THEM AND HYBRIDOMAS THEREOF**

[75] Inventors: Shuzo Sawada; Takashi Kawamura; Yasuhiko Masuho; Katsuhiko Tomibe, all of Tokyo, Japan

[73] Assignee: Teijin Limited, Osaka, Japan

[21] Appl. No.: 538,608

[22] Filed: Jun. 13, 1990

Related U.S. Application Data

[63] Continuation of Ser. No. 939,519, Nov. 12, 1986, abandoned.

[30] Foreign Application Priority Data

Mar. 11, 1985 [JP] Japan ................... 60-46445
Mar. 11, 1985 [JP] Japan ................... 60-46446
Mar. 10, 1986 [WO] PCT Int'l Appl. ... PCT/JP86/00124

[51] Int. Cl.$^5$ ............... A61K 39/40; A61K 39/104; C08B 37/00; C07K 15/28
[52] U.S. Cl. .................... 424/87; 424/85.8; 424/88; 424/92; 435/172.2; 435/172.3; 435/240.26; 435/240.27; 514/54; 530/388; 530/387; 530/808; 536/123
[58] Field of Search ............ 530/387, 388; 435/240.26, 240.27, 70.2, 172.2; 514/2, 8, 10, 21, 54; 424/85.8, 88, 91, 92; 536/123

[56] References Cited

U.S. PATENT DOCUMENTS

4,285,936  8/1981  Pier et al. .................. 424/88

FOREIGN PATENT DOCUMENTS

0101039  2/1984  European Pat. Off. .
0163493  12/1985  European Pat. Off. .
8501659  4/1985  PCT Int'l Appl. .
8404458  11/1989  PCT Int'l Appl. .

OTHER PUBLICATIONS

Braude et al., Adv. Int. Med., vol. 26, pp. 427-445 (1980).
Teng et al., PNAS (U.S.A.), 82, 1790-94 (Mar. 1985).
Kirkland et al., Journal Immunol., 132(5), 2590-3 (May, 1984).
Sawada et al., J. Inf. Dis., 152(5), 965-70 (Nov. 1985).
MacIntyre et al., Inf. Immun., 52(1), 76-84 (Apr. 1986).
Pier et al., Inf. Immun., 22(3), 908-18, 919-25 (Dec. 1978).
Pollack et al., J. Clin. Invest. 63, 276-86 (Feb. 1979).
Hiernaux et al., Eur. J. Immunol., 12, 797-803 (1982).
Hancock et al., Inf. Imm., 37(1), 166-71 (Jul. 1982).
CA 98-213852q, Rowe et al., "Structure of the core oligosaccharide from the lipopolysaccharide of *Pseudomonas aeruginosa* PAC1R and its defective mutants", Eur. J. Biochem., 132, pp. 329-37 (1983).
Mutharia et al., "Monoclonal antibodies specific for *E. coli* J5 lipopolysaccharide: cross-reaction with other gram-negative bacterial species"; Infection and Immunity, 45, pp. 631-36 (1984).
CA 94-63513f, Knirel et al., "Bacterial antigenic polysaccharides, 11, Structure and carbon-13 NMR spectrum of O-specific polysaccharide from *Pseudomonas cepacia*", Bioorg. Khim., 6, pp. 1851-9 (1980).
CA 87-100398a, Horton et al., "Analytical characterization of lipopolysaccharide antigens form seven strains of *Pseudomonas aeruginosa*", Carbohydr. Res., 55, pp. 35-47 (1977).

*Primary Examiner*—Sam Rosen
*Assistant Examiner*—Jeff Kushan
*Attorney, Agent, or Firm*—Sughrue, Mion, Zinn, Macpeak & Seas

[57] ABSTRACT

*P. aeruginosa* E87Ag antigen comprising polysaccharide fraction with molecular weight of about 27,000 which is contained in lipopolysaccharide of *P. aeruginosa*; anti-*P. aeruginosa* human or mouse monoclonal antibody which recognizes said E87Ag antigen; and mouse-human or mouse-mouse hybridoma which produces said monoclonal antibody.

The monoclonal antibody can be used for making diagnosis and therapy of infections with *P. aeruginosa*.

10 Claims, 5 Drawing Sheets

E87AG ANTIGENS OF *PSEUDOMONAS AERUGINOSA* AND MONOCLONAL ANTIBODIES AGAINST THEM AND HYBRIDOMAS THEREOF

This is a continuation of application No. 06/939,519 filed Nov. 12, 1986 now abandoned.

TECHNICAL FIELD

The present invention relates to specific antigens possessed by *Pseudomonas aeruginosa* and monoclonal antibodies against such antigens and a process for the preparation thereof. Furthermore, this invention relates to hybridomas which produce said monoclonal antibodies and a herapeutic agent for *Pseudomonas aeruginosa* infections which contains said monoclonal antibodies as the effective ingredient. It is therefore an object of this invention to provide anti-*P. aeruginosa* monoclonal antibodies to be used for the diagnosis and treatment for *Pseudomonas aeruginosa* infections or specific types of *P. aeruginosa* antigens which can be used for making vaccines to prevent humans or animals from Pseudomonas aeruginosa infections.

BACKGROUND OF THE ART

*P. aeruginosa* was originally a kind of bacterium having low pathogenecity; however, as a result of the proliferative replacement of bacteria due to the general administration of antibiotic drugs, infectious diseases arising from drug resistant *P. aeruginosa* have recently been increasing in immunodeficient patients, especially those with cystic fibrosis, diffuse panbronchiolitis (DPB), thermal burns, and cancer and the patients are often found falling in a serious condition. For treating a patient with *P. aeruginosa* infectious disease properly, early diagnosis is of imperative necessity, and such diagnosis requires a monoclonal antibody which can detect *P. aeruginosa* rightly, which further requires an antigen specific to *P. aeruginosa* for preparing said antibody. The development of *P. aeruginosa* antigen which has high immunogenecity with less side effects and can be used as a vaccine for humans and animals, for instance, a mink, against *P. aeruginosa* infections is also desired. Furthermore, in the treatment of *P. aeruginosa* infections there is a problem that the use of antibiotic drugs are not always sufficiently effications because there are many cases where *P. aeruginosa* is drug resistant and some cases where the patient suffers from a weakened immune response. Research has accordingly been conducted concerning the immunotherapy by use of anti-*P. aeruginosa* antibodies, especially its monoclonal antibodies, but no methods have yet been developed to such an extent as to be clinically useful.

As the surface antigens of *P. aeruginosa*, lipopolysaccharide (LPS), outer membrane protein (OMP), flagella, pili, and polysaccharide arising from the slime are known. Of these surface antigens, LPS has a polysaccharide O side chain which determines the serotype of *P. aeruginosa* and there are 16 kinds of serotypes (according to Homma's classification) ranging from 1 to 16 known presently. LPS also has a core region and lipid A besides the O side chain. Lipid A is buried inside the outer membrane of *P. aeruginosa*, from which the core region extends outside the outer membrane through 2-keto-3-deoxyoctonate and the O side chain extends from the core region further outside. It is known that an antibody to LPS can be readily produced in humans and animals and has protective potencies against infections. There are, however, problems that this O side chain of LPS has the serotype specificity and that LPS itself is poisonous to the living body.

Attempts have been made to obtain a polysaccharide chain antigen having high immunogenecity with no toxicity from LPS of *P. aeruginosa*. Japanese Patent Laid-Open Publication No.175440/'84, for instance, describes that a polysaccharide antigen with a molecular weight of 5,000 to 40,000 having no endotoxin activity can be obtained by removing lipid A from LPS of *P. aeruginosa* by treatment with acetic acid. This type of antigen has polysaccharide O side chain and accordingly still retains the serotype specificity.

Japanese Patent Laid-Open Publication No.29622/'84 discloses that a hybridoma, which is deemed to recognize O side chain and produce monoclonal anti-*P. aeruginosa* mouse antibody, is obtained by cloning a hybridoma (fused cell) which is prepared by fusion of spleen cells of a BALB/C mouse immunized with LPS of *P. aeruginosa* (antibody producing cells) with mouse myeloma cells (P3-X63-Ag8-U1 strain).

The antibody to O side chain of LPS offers a problem of having its scope of application limited depending upon the object of therapy and diagnosis because of the serotype specificity. It is more advantageous and safe to use anti-*P. aeruginosa* human antibody of the homogeneous protein for therapy of or making a diagnosis of human diseases, and this raises the necessity of establishing a mouse-human hybridoma or a human-human hybridoma by use of antibody producing human cells. Different from the case of animals, however, the case of using human cells involves another problem of difficulty in the collection and treatment of appropriate antibody producing cells since it is not possible to adopt a method in which men are immunized with a large amount of *P. aeruginosa* or their surface antigens and then effectively stimulated antibody producing cells are collected and used for cell fusion, and accordingly, no report has yet been made as to definitely successful cases.

DISCLOSURE OF THE INVENTION

The present inventors have conducted intensive research with the purpose of finding specific antigens of *P. aeruginosa* having less serotype specificity and no endotoxic activity and also finding monoclonal antibodies which will react with as many types of *P. aeruginosa* as possible regardless of serotypes. The result of the investigation made on monoclonal antibodies produced by hybridomas obtained by fusing mouse myeloma cells with antibody producing cells, which have been collected from the mice immunized with various types of *P. aeruginosa*, has led to a finding that the monoclonal antibody, which is obtained in a case where *P. aeruginosa* IFO 3080 strain (serotype M) is used, effectuates a cross reaction with various types of *P. aeruginosa* regardless of their serotypes. The specific properties of this monoclonal antibody and the antigen were further studied to complete the present invention.

The present invention relates to an E87Ag antigen of *P. aeruginosa* which is contained in the lipopolysaccharide of *P. aeruginosa* and comprises a polysaccharide of molecular weight of about 27,000 (25,000 to 35,000) having neutral sugar, especially rhamnose, as the main structural unit; a monoclonal antibody (hereinafter referred to as monoclonal antibody E87) to said antigen; and a hybridoma productive of such antibody.

BEST MODE OF CARRYING OUT THE INVENTION

Antigen E87Ag of this invention is obtained by hydrolyzing LPS of *P. aeruginosa* with a weak acid, removing the formed lipid A, and subjecting acid treated polysaccharide (A-PS) void of said lipid A to gel filtration to isolate and collect polysaccharide antigens with a molecular weight of about 27,000 (25,000 to 35,000) consisting mainly of neutral sugar.

LPS of *P. aeruginosa* is prepared from IFO 3080 strain or PAO1 strain of *P. aeruginosa* by any publicly known method. Lipid A is severed when LPS is hydrolyzed with a weak acid such as acetic acid. It is deemed that at this time the antigen E87Ag of this invention is also severed from the polysaccharide O side chain. Lipid A is eliminated after the precipitation by centrifugation. Thereafter, A-PS is subjected to gel filtration by means of Sephadex or Sephacryl. For instance, A-PS is subjected to Sephadex 50, its void volumes are collected, and then E87Ag antigens of this invention is obtained by gel filtration carried out with Sephacryl S-300.

The monoclonal antibody and the hybridoma productive of it proposed by this invention can be obtained by generally known technique of cell fusion.

It is a publicly known method to establish a hybridoma strain, which continues to produce and secrete monoclonal antibodies for all time, by fusing lymphocytes or B cells (antibody producing cells), which produce specific antibodies but are destined to perish in course of time, with myeloma cells, which continue to proliferate for all time in the incubator, according to the technique of cell fusion. It is also a known technique to obtain monoclonal anti-*P. aeruginosa* antibodies from hybridomas which are productive of anti-*P. aeruginosa* antibodies by cloning the fused cells prepared by fusing the anti-*P. aeruginosa* antibody producing cells with the myeloma cells.

In this invention, the preparation of anti-*P. aeruginosa* mouse monoclonal antibodies starts with the cell fusion between antibody producing cells of mice immunized with *P. aeruginosa* IFO 3080 or E87Ag antigens and mouse myeloma cells to give hybridomas.

As the mouse myeloma cells, it is advantageous to use 8-azaguanine resistant cell lines and among those publicly known ones, there are P3-X63-Ag8, P3-X63-Ag8-U1, P3-NS1/1-Ag4-1, P3-X63-Ag8-6.5.3, SP2/O-Ag14, FO, and MPC11-45.6 TG 1.7 of BALB/C mice.

Cell fusion can be carried out according to a publicly known method. For instance, antibody producing cells and myeloma cells are mixed at a ratio of 10:1 to 1:10, preferably at a ratio of 1:1 to 1:3. An appropriate cell fusion mixture such as RPMI 1640 containing about 35% polyethylene glycol (molecular weight approximately 1,000–6,000) and about 7.5% dimethyl sulfoxide is added to the cell mixture and are stirred for one to several minutes at room temperature to 37° C. Therefore the mixture is diluted little by little with RPMI 1640 containing 10% FCS, washed, and adjusted to have cell concentration of 1 to $5 \times 10^5$ cells/ml by use of a selective liquid culture medium HAT (hypoxanthine-aminopterin-thymidine). Thus prepared culture liquid was added to a 96-well plate, for instance, in portions of 0.2 ml per well, and cultured in 5% $CO_2$ air at 35°–38° C. for 2 to 3 weeks. In the HAT liquid culture medium, only hybridomas can survive and 8-azaguanine resistant myeloma cells and fused cells between myeloma cells can not survive (unfused antibody producing cells perish in a course of several days). Then from the colonies of hybridoma, only those hybridomas that secrete monoclonal antibodies reactive against *P. aeruginosa* IFO 3080 or E87Ag antigens are selected. This process of selection (or screening) can be carried out by subjecting the mouse monoclonal antibodies produced by hybridomas different from each other to the enzyme-linked-immunosorbent assay (ELISA) by use of plates fixed with LPS of IFO 3080 or E87Ag antigens.

The anti-*P. aeruginosa* mouse monoclonal antibody of this invention has a characteristic of binding not only to *P. aeruginosa* IFO 3080 which is used in the immunization but also to about 70% of Homma serotype standard strains. This antibody has a characteristic feature of recognizing LPS of *P. aeruginosa* as described later, especially recognizing the neutral sugar of molecular weight of about 27,000 (25,000 to 35,000) which constitutes part of the LPS. It has been made known that the isotype of this antibody is IgG2a.

In this invention, anti-*P. aeruginosa* human monoclonal antibodies are obtained by preparing mouse-human hybridomas from anti-*P. aeruginosa* antibody producing human cells and mouse myeloma cells; culturing these hybridomas and/or cell lines arising from them; and collecting the resultant human monoclonal antibodies, which have a property to bind to *P. aeruginosa* E87Ag antigens, from the culture.

What is referred to as antibody producing human cells in this invention are human lymphocytes (or B cells) which are capable of secreting antibodies. They are found among the cells of the spleen, lymph node, peripheral blood, bone-marrow, tonsils, and adenoids. For carrying out the object of this invention, lymphocytes may be taken from any sources; however, the desirable ones are those collected from the tonsils and spleen. As the mouse myeloma cells, those mentioned previously can be used.

In this invention, *P. aeruginosa* such as *P. aeruginosa* IFO 3080 that has an antigen E87Ag is used. Firstly, human lymphocytes taken from the tissues of tonsils, lymph node, spleen, or peripheral blood are prepared as mononuclear cells. The mononuclear cells are then cultured in the presence or absence of mitogen such as pokeweed mitogen for 5 to 7 days in a 5% $CO_2$ incubator and the antibodies in the culture supernatant were determined by ELISA on a plate fixed with said *P. aeruginosa* to select the tissues that contained desirable mononuclear cells. Next, the cell fusion between the lymphocytes of the thus selected tissues and the myeloma cells was effected to establish heterogeneous colonies of hybridomas. The cell fusion can be carried out in the same way as mentioned previously.

The anti-*P. aeruginosa* monoclonal antibodies of this invention not only strongly bind to *P. aeruginosa* IFO 3080 but also bind to about 70% of Homma serotype standard strains and furthermore bind to most of the *P. aeruginosa* obtained from patients with cystic fibrosis (see Infection and Immunit., 1983, vol.42, pp 170-177) or DPB mainly caused by *P. aeruginosa*, whose serotype can not be classified by Homma serotype, and hence can be considered nontypable. Also, these antibodies have a characteristic feature of recognizing LPS of *P. aeruginosa*, especially the neutral sugar with molecular weight of about 27,000 (25,000–35,000) consisting mainly of rhamnose to compose LPS as described later.

EXAMPLE 1

BALB/C mice were immunized by intraperitoneal injection of $1 \times 10^7$ cells of formalin-treated *P. aeruginosa* strain IFO 3080 once a month for 5 months. Four days after a booster immunization by intravenous injection of the same dose of cells, the mice were killed, and their spleen cells were fused with mouse myeloma cells P3-X63-Ag8-U1 (hereinafter abbreviated to P3U1). This was cultured in 192 wells and hybridomas grew in 168 wells. The culture supernatants in the wells where hybridomas grew were tested by ELISA and 16 wells were found reacting to *P. aeruginosa* strain IFO 3080. Some of these culture supernatants were found not only binding to *P. aeruginosa* strain IFO 3080 used in the immunization but also cross-reacting with several of Homma serotype standard strains. The result of the cross reaction of the typical wells to Homma strains is shown in Table 1. Among these hybridomas, E8 which strongly reacted with the largest number of different serotypes was cloned twice by limiting dilution to obtain monoclonal antibody E87 (and the hybridoma which produces this monoclonal antibody was named E87 which has been deposited at the ATCC receiving accession number HB 9189).

The serotype of *P. aeruginosa* were determined by use of anti-*P. aeruginosa* anti-serum supplied by Denka Seikensha.

TABLE 1

| Homma strain (Serotype) | ELISA optical density reading* | | | | | |
|---|---|---|---|---|---|---|
| | C2 | E1 | E4 | E8 | D10 | F8 |
| ATCC 27577 (A) | 0.6 | 0.4 | 0 | 0.3 | 0 | 0.1 |
| 27578 (B) | 0.3 | 0.2 | 0 | 0.1 | 0 | 0 |
| 27579 (C) | 0 | 0 | 0 | 0 | 0 | 0 |
| 27580 (D) | 0.8 | 0.5 | 0.1 | 0.8 | 0.1 | 0.5 |
| 27581 (E) | 0 | 0 | 0.4 | 0 | 0 | 0 |
| 27582 (F) | 0.6 | 0.4 | 0.8 | 0.4 | 0 | 0.2 |
| 27583 (B) | 0.5 | 0.4 | 0 | 0.4 | 0 | 0 |
| 27584 (G) | 0.6 | 0.3 | 0 | 0.3 | 0 | 0 |
| 27585 (H) | 0.8 | 0.5 | 0 | 0.5 | 0.1 | 0 |
| 27586 (I) | 0.7 | 0.4 | 0 | 0.5 | 0 | 0 |
| 27587 (J) | 0 | 0 | 0 | 0 | 0 | 0 |
| 27588 (K) | 0.4 | 0.2 | 0 | 0.4 | 0 | 0 |
| 27589 (B) | 0 | 0 | 0 | 0 | 0 | 0 |
| 27590 (L) | 0.2 | 0.1 | 0 | 0.1 | 0 | 0 |
| IFO 3080 (M) | 0.9 | 0.6 | 0.2 | 1.5 | 0.2 | 0.3 |

*Formalin-killed $5 \times 10^6$ cells were fixed to a polystyrene plate and 100 μl of 2-day culture supernatant of $5 \times 10^5$ hybridomas/ml was added to be incubated. Then anti-mouse IgG antibodies labeled with alkaline phosphatase (Tago, Burlingame, Calif.) were added as secondary antibodies to conduct ELISA. The figures in the table indicate optical density readings at 405 nm 30 minutes after the addition of the substrate.

EXAMPLE 2

The hybridoma secreting antibody E87 was further cultured in 1 liter of serum-free RDF-TES culture medium (see Proc. Natl. Acad. Sci. USA, 1982; Vol.79, pp 1158-62). The liquid culture medium was concentrated to 30 ml by use of the molecular sieve membrane (PM-30; Amicon Corp.). The concentrate was subjected to chromatography on DEAE - Sephacryl after having been dialyzed against 20 mM sodium phosphate buffer solution (pH 7.2). Antibody E87 was eluted the unadsorbed fractions were recovered as a precipitate upon concentration by PM-30. The recovered antibody E87 gave two bands in the 10% SDS acrylamide gell electrophoresis to show that the respective molecular weights corresponded to the H chain and L chain of IgG.

The concentration of the antibody E87 was determined by ELISA with use of a kit for the quantitative determination of mouse immunoglobulin G (Miles Laboratories) or a plate coated with goat antibody to mouse IgG (Cappel Laboratories).

The isotype of antibody E87 was determined to be IgG2a by ELISA with use of rabbit anti-mouse isotype antibodies (Nordic Immunology).

EXAMPLE 3

The binding specificity of the antibody E87 to *P. aeruginosa* was tested by ELISA with use of fifty-five *P. aeruginosa* strains of various serotypes. The result is shown in Table 2. The antibody E87 reacted with 44 strains out of the 55 strains and was found binding to the wide range of *P. aeruginosa* disregarding serotypes.

TABLE 2

| Strain | Serotype | ELISA O.D. (E87) | Strain | Serotype | ELISA O.D. (E87) |
|---|---|---|---|---|---|
| C-8 | A | 0.5 | 1128 | F | 0 |
| N-1 | A | 1.7 | 146 | F | 1.2 |
| 122 | A | 0.6 | 28 | F | 1.0 |
| O-34 | A | 1.4 | O-1 | G | 0 |
| 97 | B | 0 | O-3 | G | 0 |
| 1130 | B | 0.5 | O-8 | G | 0.4 |
| 1120 | B | 0.5 | O-11 | G | 0.4 |
| Tid30 | B | 0.2 | O-23 | G | 0 |
| IFO3445 | B | 0.5 | O-31 | G | 0 |
| PA0-1 | B | 0.7 | O-36 | G | 0.2 |
| C19 | B | 0 | O-38 | G | 0 |
| 119 | B | 0 | O-7 | G | 0.8 |
| N-3 | C | 0.9 | O-19 | G | 0.6 |
| 20 | C | 0.6 | 5 | G | 0.4 |
| N26 | C | 1.3 | Fisher-IT-1 | G | 0.8 |
| 142 | C | 0.8 | 1133 | H | 1.1 |
| O-56 | E | 1.1 | O-64 | H | 1.6 |
| O-100 | E | 1.0 | O-22 | H | 1.2 |
| O-101 | E | 1.0 | 1258 | H | 1.4 |
| 1127 | E | 0 | 38 | I | 1.8 |
| 1237 | E | 0.1 | 1263 | I | 1.4 |
| 1260 | E | 0.1 | O-25 | I | 1.2 |
| C-12 | E | 1.0 | O-50 | I | 1.8 |
| N-2 | E | 1.1 | C9 | M | 1.1 |
| Fisher IT-2 | E | 1.0 | C14 | M | 0.4 |
| O-32 | F | 1.0 | O-24 | M | 1.1 |
| 64 | F | 1.7 | IFO3080 | M | 1.9 |
| O-102 | F | 0 | | | |

EXAMPLE 4

The cross-reactivity of antibody E87 was tested by ELISA with use of various kinds of cell lines belonging to gram-negative bacteria. The result of the test is shown in Table 3.

TABLE 3

| Bacterial strain | | ELISA O.D.* (E87) |
|---|---|---|
| *P. cepacia* | GIFU 518 | 0 |
| | GIFU 644 | 0 |

TABLE 3-continued

| Bacterial strain | | ELISA O.D.*(E87) |
|---|---|---|
| | GIFU 10015 | 0 |
| | GIFU 2918 | 0 |
| | GIFU 10014 | 0 |
| | GIFU 10016 | 0 |
| | GIFU 1709 | 0 |
| | GIFU 10017 | 0 |
| | GIFU 1116 | 0 |
| | GIFU 2162 | 0 |
| P. maltophilia | GIFU 680 | 0 |
| | GIFU 710 | 0 |
| | GIFU 1034 | 0.4 |
| | GIFU 1168 | 0.8 |
| | GIFU 1174 | 0 |
| | GIFU 2491 | 0 |
| P. putida | IAM 1505 | 0 |
| | IAM 1506 | 0 |
| P. saccharophilia | IAM 1504 | 0 |
| P. reptilivora | IFO 3461 | 0 |
| P. taetrolens | IAM 1653 | 0.2 |
| P. rubescens | IAM 1510 | 0 |
| P. aureofaciens | IAM 12353 | 0.4 |
| P. synxantha | IAM 12356 | 0 |
| Salmonella minesota 1114 | Smooth | 0 |
| | R 60 (Ra) | 0 |
| | R 345 (Rb) | 0 |
| | R 5 (Rc) | 0 |
| | R 7 (Rd1) | 0 |
| | R 4 (Rd2) | 0 |
| | R 595 (Re) | 0 |
| Esherichia coli | K 12 | 0 |
| | NIHJ-JC-2 | 0 |
| Proteus morganii | IFO 3848 | 0 |
| Proteus moriabilis | IFO 3849 | 0 |
| Proteus vulgarie | ox-19 | 0 |
| Klebsiella pneumoniae | PCI-602 | 0 |
| Serratia marcescens | IAM 1184 | 0 |
| Bacillus subtilis | ATCC 6633 | 0 |
| Staphylococcus aureus | 209 P | 0 |

*Formalin-killed 5 × 10$^6$ whole cells were fixed to a polystyrene plate; 1 μg of antibody E87 was added and incubated; and anti-mouse IgG antibodies labeled with alkaline phosphatase (Tago, Burlingame, Calif.) were added as secondary antibodies to be subjected ELISA. The figures in the table indicate optical density readings at 405 nm 60 minutes after the addition of the substrate.

The antibody E87 reacted with two strains of Pseudomonas maltophilia, P. taetrolens, and P. aureofaciens, but did not utterly react with all the other strains including two strains of gram-positive bacteria.

EXAMPLE 5

(1) Preparation of LPS and treatment of LPS with acetic acid

When P. aeruginosa were cultured in 10 l of L-broth medium until the late logarithmic growth phase, formaldehyde was added to the culture medium up to a 0.3% concentration to kill the cells. The cells were collected by centrifugation, washed once with distilled water, and freeze-dried. LPS was extracted by the method described by Johnson and Perry (Can. J. Microbiol., 1976, vol.22, pp 29-34). Acetic acid-treated LPS (A-PS) was prepared by suspending LPS in 1% acetic acid, carrying out the hydrolysis at 100° C. in a sealed tube for 2 hours, and the resulting lipid A was removed by centrifugation. The centrifugal supernatants were collected, dialyzed against distilled water, and lyophilized to obtain the desired acetic acid-treated LPS (A-PS).

The purity of LPS prepared from P. aeruginosa PAO1 and IFO 3080 was high, both containing only 0.3% (w/w) or less protein and 0.25% (w/w) or less nucleic acid. The yield of LPS from P. aeruginosa strain PAO1 was 35 mg from 1 g of dry weight cells in aqueous phase and 3.5 mg of LPS was recovered from 1 g dry weight of strain IFO 3080 in aqueous phase.

(2) Reaction with LPS

The reactivity of E87 antibody to LPS of P. aeruginosa was examined to check whether this antibody recognizes LPS. 100 μl of LPS suspension (10 μg/ml) was dispensed into the 96-well flat polyvinyl chloride plates and held overnight at room temperature. After the LPS suspension was removed, the plates were washed three times with PBS and the wells were filled with PBS containing 0.5% bovine serum albumin, and incubated for 3 hours at room temperature. After the removal of PBS, 100 μl of antibody E87 (10 μg/ml) was added to the culture and ELISA was carried out.

The result is shown in Table 4. It was found that antibody E87 reacted with LPS of ATCC 27577, 27584, 7586, 64 and PAO1 but not with that of ATCC 27581 and 97.

TABLE 4

| Homma strain | Serotype | ELISA O.D. reading* |
|---|---|---|
| ATCC 27577 | A | 1.0 |
| ATCC 27581 | E | 0 |
| ATCC 27584 | G | 2.1 |
| ATCC 27586 | I | 2.0 |
| 64 | F | 2.2 |
| PAO1 | B | 2.2 |
| 97 | B | 0 |

*The figures in the table indicate optical density readings at 405 nm 60 minutes after the addition of the substrate.
ELISA was carried out with use of polyvinyl chloride plates fixed with LPS where 1 μg of antibody E87 was added.

(3) Binding inhibition activity test

Figure 1:
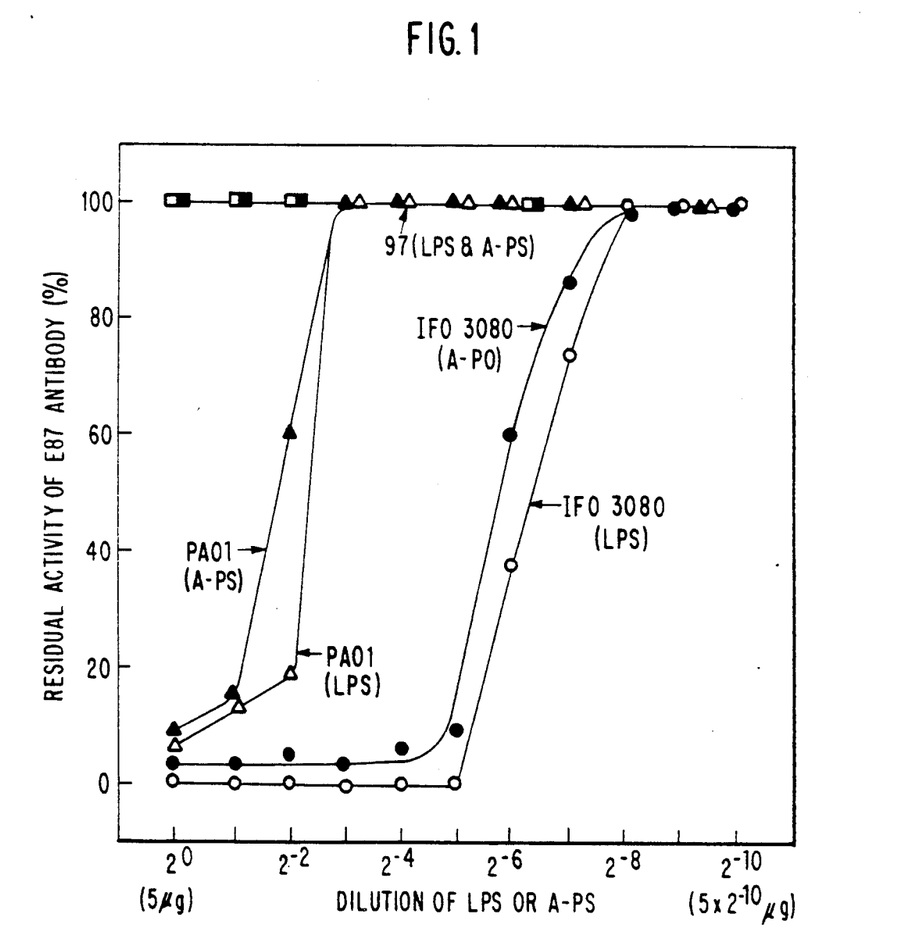
FIG. 1 is a drawing to show the degree of inhibition of the activity of monoclonal antibody E87 by LPS or A-PS.

The analysis of inhibition assay (by ELISA) was carried out to test whether the binding of antibody E87 to PAO1 or IFO 3080 cells is blocked by LPS and A-PS or not so that the interaction between antibody E87 and LPS and A-PS of P. aeruginosa might be clarified. The result is shown in FIG. 1. Strong blocking activity was seen when LPS and A-PS of IFO 3080 was used as inhibitor and in the case of PAO1 blocking was also seen, though somewhat weaker than IFO 3080; however, no blocking activity was observed in both LPS and A-PS of 97 even when the maximum quantity of 5 μg of these fractions was added. The blocking activities calculated in terms of concentrations (ID$_{50}$) needed for LPS and A-PS to give 50% blocking showed that IFO 3080 had 2$^4$ times higher blocking activity than PAO1. It is understood from this fact that antibody E87 recognizes the antigens contained in common in both LPS and A-PS.

(4) Analysis of antigens by chromatography (1)

Figure 2:
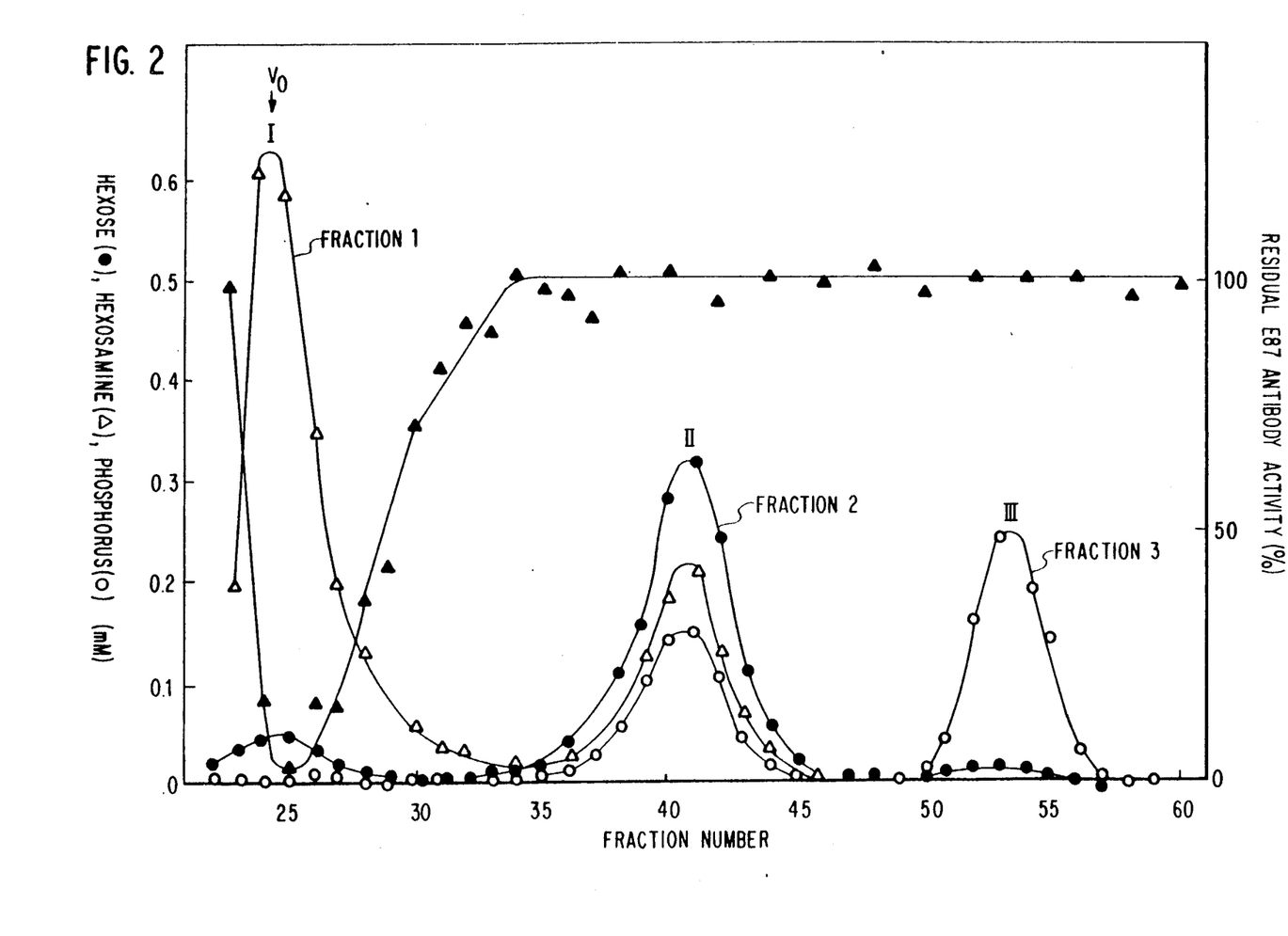
FIG. 2 shows elution profiles of A-PS of PAO1 on Sephadex G-50 column.

With the object of analyzing the antigens existing in A-PS which antibody E87 recognizes, 16 mg of A-PS of PAO1 (serotype B) was eluted from Sephadex G50 column with 50 mM pyridine-acetate buffer (pH 4.3). By monitering hexosamine, hexose, and phosphorus, 3 fractions different in molecular weight were obtained. The result is shown in FIG. 2.

Incidentally, hexose was determined colorimetically by anthrone reaction (Ind. Eng. Chem. Anal. Ed., 1946, vol. 18, p. 449) in amount converted to glucose. Hexosamine was determined by the method proposed by Tsuji et al. (Chem. Pharm. Bull. (Tokyo), 1967, vol. 17, pp 1505-1510) with use of glucosamine as standard substance. Phosphorus was determined by the method of Lowry et al. (J. Biol. Chem., 1954, vol. 207, pp 1-17).

Fraction 1 was eluted in the void volume, mainly contained hexosamine, and a small peak of hexose was observed. Fraction 2 was made up of hexose, hexosamine, and phosphorus. A high peak of phosphorus appeared in fraction 3 and 2-keto-3-deoxyoctonate was also eluted in this fraction 3. The same inhibition assay as described in the preceding (3) was also made and it was found that the inhibitory substance of binding activity of antibody E87 also existed in fraction 1 (see △ mark in FIG. 2).

Figure 3:
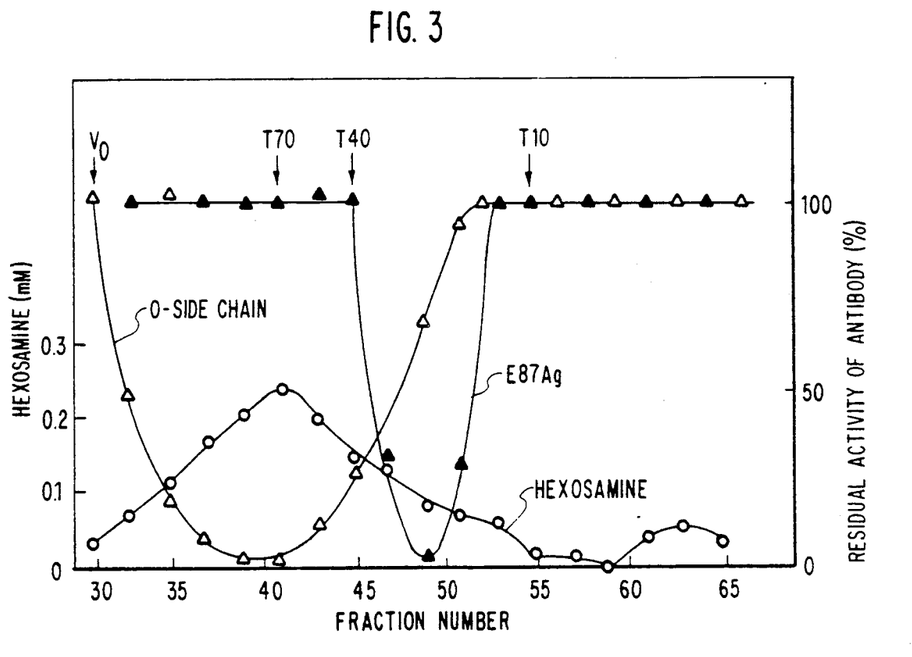
FIG. 3 shows elution profiles of O side chain antigen obtained from PAO1 and E87Ag antigen on Sephacryl S-300 column.

Fraction 1s were collected and pooled to be dialyzed against PBS (pH 7.2) and lyophilized. The lyophilized specimen (10 mg) was subjected to Sephacryl S-300 column chromatography and the adsorbed fractions were eluted with PBS (pH 7.2) to see if the O side chain antigen and the antigen which antibody E87 recognizes (E87Ag antigen) would separate or not. The result is shown in FIG. 3. As seen apparently from FIG. 3, the elution peak of hexosamine and that of O side chain antigen were almost in the same position. The elution peak of the O side chain antigen was determined by ELISA with use of the rabbit anti-P. aeruginosa (serotype B) antibody (Denka Seikensha). Antigen E87Ag was eluted in the fractions for lower molecular sizes than the O side chain antigen and its peak was much sharper than the peak of the O side chain. The aforementioned fact tells that antigen E87Ag differs from the O side chain antigen.

(5) Analysis of antigens by chromatography (2)

Figure 4:
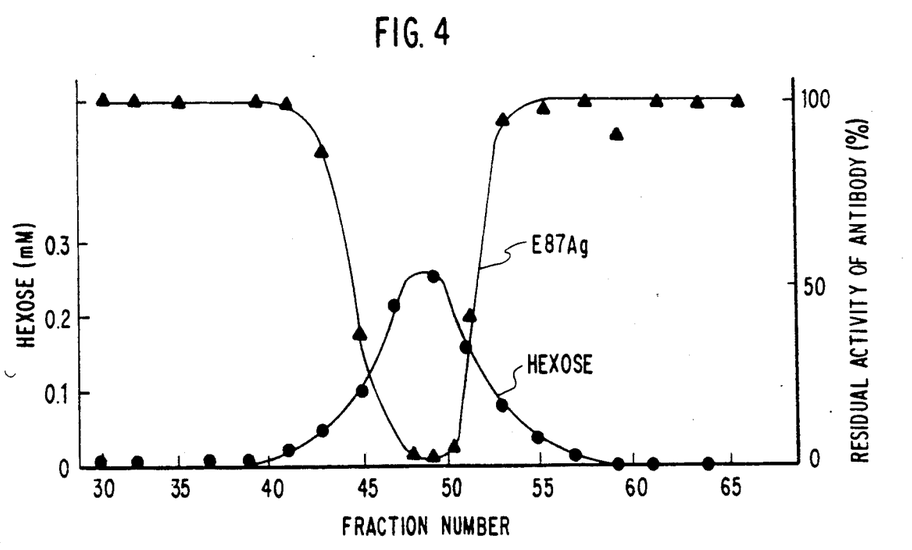
FIG. 4 shows elution profiles of E87Ag antigen obtained from IFO 3080 on Sephacryl S-300 column.

Eight miligrams of A-PS of IFO 3080 obtained in the aforementioned (1) was eluted from Sephadex G-50 columns with 50 mM pyridine-acetate buffer, pH 4.2, and a substance which inhibits the antibody activity of antibody E87 was eluted in the void volume (fraction 1). Fractions 1 were pooled, dialyzed, lyophilized, and the lyophilized substance was put to Sephacryl S-300 column chromatography. Its elution profile is shown in FIG. 4. The figure shows that the substance which inhibits the antibody activity of antibody E87 is eluted in the same peak as E87 antigen of PAO1 and that it eluted in the same peak as the neutral sugar (hexose).

It is therefore apparent that antigen E87Ag, which antibody E87 recognizes, exists in the neutral sugar fraction of A-PS.

Dextrans T70, T40, and T10 (Pharmacia Fine Chemical) were used as molecular weight markers to determine the elution peaks of the respective molecular weight markers (see FIG. 3) beforehand and from the relative positions of their elution peaks the molecular weight of antigen E87Ag was calculated to be approximately (27,000 (25,000-35,000).

EXAMPLE 6

Colorimetric determinations were conducted to determine the sugar composition of antigen E87Ag. The result is shown in Table 5, from which it is made known that it consists mainly of methylpentose (a kind of hexose).

The anthone-sulfuric acid reaction shows the existence of hexose (hexose neutral sugar), carbazole-sulfuric acid reaction shows the presence of acid sugar mainly comprising uronic acid, cysteine-sulfuric acid reaction shows the existence of methylpentose (neutral sugar) which is a kind of hexose, orcinol-sulfuric acid reaction shows the existence of pentose (pentose neutral sugar), and MBTH method shows the existence of hexosamine (basic sugar).

TABLE 5

| Colorimetric Determination | Mole ratio |
| --- | --- |
| Anthrone-sulfuric acid reaction 1) | 0.4 |
| Carbazole-sulfuric acid reaction 2) | ND 6) |
| Cysteine-sulfuric acid reaction 3) | 1.0 |
| Orcinol-sulfuric acid reaction 4) | 0.1 |
| MBTH (3-methyl-2-benzothiazolinone 5) hydrazone hydrochloride) method | 0.03 |

1) Ind. Eng. Chem. Anal. Ed., 1946, vol. 18, p. 119.
2) Anal. Biochem., 1968, vol. 24, pp. 470-481.
3) J. Biol. Chem., 1948, vol. 175, pp. 595-603.
4) Zeitshnift für Physiologishe Chemie, 1939, vol. 258, pp. 117-120.
5) Chem. Pharm. Bull. (Tokyo), 1969, vol. 17, pp. 1505-1510.
6) Value outside the limit of measurement.

EXAMPLE 7

The sugar composition which constitute E87Ag was studied by thin-layer chromatography. 30 µg of E87Ag antigen was subjected to hydrolysis with 2N hydrochloric acid at 100° C. for two hours in a sealed tube and hydrochloric acid was removed by evaporation to dryness. The residue was dissolved in a slight amount of water and put to cellulose thin-layer chromatography. The solvent made up of 1-butanol, pyridine, acetic acid, and water at a mixing ratio by volume of 60:40:3:30 was used.

Figure 5:
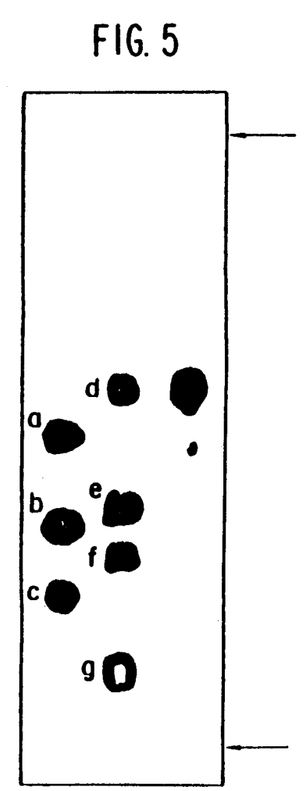
FIG. 5 shows thin-layer chromatogram of E87Ag antigen.

The result is shown in FIG. 5 (color was developed with alkaline silver nitrate). In FIG. 5, the arrows indicate the origin and the solvent front. On the left and middle lanes are standard substances, each being a=ribose, b=glucose, c=glucosamine, d=rhamnose, e=arabinose, f=galactose, and g=glucuronic acid. E87Ag antigen is spotted on the right lane, being in accord with the standard substance like ribose.

Accordingly it has been made clear that E87Ag antigen mainly comprises rhamnose (a kind of methylpentose)

EXAMPLE 8

Figure 7:
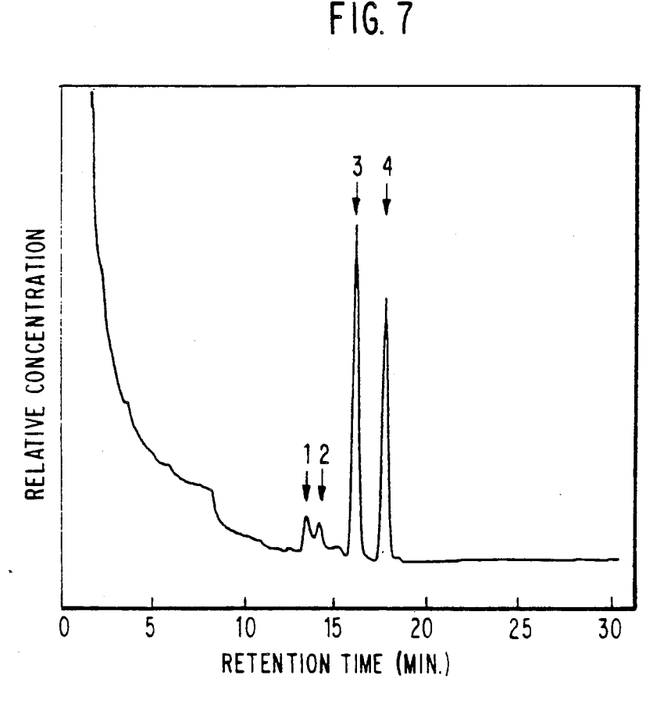
FIG. 7 shows the result of gas chromatography of E87Ag antigen.

E87Ag was subjected to gas chromatography to have its sugar composition studied. After the hydrolysis of 15 µg of E87Ag antigen carried out at 100° C. for 1 hour with use of 1N hydrochloric acid in a sealed tube, hydrochloric acid was removed by evaporation to dryness. 3 µl of a mixture consisting of pyridine, hexamethyldisilazane, and trimethylchlorisilane (at a ratio by volume of 4:2:1) was added to the residue and the admixture was agitated vigorously for 1 minute to make the sugar into a trimethylsilyl derivative and 2 µl of the reaction liquid was subjected to gas chromatography (GC-7AG manufactured by Tsushima Seisakusho). The column was 1.5 m and filled with 3% silicone SE52 resin and the temperature was raised from 100° C. up to 250° C. at a rate of 4° C./min. The result is shown in FIG. 7. The figures indicate the respective peaks. The standard substances and their retention time were glucose (22.72, 25.09 min), galactose (21.27, 22.04, 23.11 min ), mannose (20.75, 23.02 min), fuxose (17.03, 17.98 min), quinovose (18.91, 20.37 min), rhamnose (16.02, 17.57 min), ribose (16.49 min), arabinose (15.74, 16.46 min), xylose (17.59, 1906 min), lyxose (15.47, 16.62 min), and sorbitol (23.86 min). The retention time of E87 antigen specimen ranged from peak 1 (13.34 min), peak 2(14.07 min), peak 3 (16.00 min), to peak 4 (17.56 min), of which peak 3 and peak 4 accorded with the standard substance rhamnose.

From the abovementioned result, it is apparent that E87Ag antigen is composed mainly of rhamnose and partly of unknown substances (in peak 1 and peak 2) in an amount of about 10% by weight.

EXAMPLE 9

(1) Selection of cells productive of anti-*P. aeruginosa* antibody

Eight lots of tonsils were obtained from eight patients with tonsillitis, from which mononuclear cells were prepared by use of Ficoll-Paque. The mononuclear cells were suspended in the culture medium A (RPMI 1640+10% fetal bovine serum+2 mM glutamine+1 mM pyrubic acid+0.02 mg/ml serine+80 μg/ml gentamicin) at a cell concentration of $5 \times 10^6$ cells/ml, to which pokeweed mitogen (PWM) was added to make a concentration of 20 μg/ml. This specimen was put in the culture plates in portions of 200 μl and cultured for 6 to 7 days in the $CO_2$ incubator (5% $CO_2$). Thereafter 100 μl of the respective culture supernatants were transferred to the plates coated with *P. aeruginosa* IFO 3080 and subjected to ELISA. Only one of the whole lots strongly reacted to *P. aeruginosa* IFO 3080. the mononuclear cells of this lot were used in the cell fusion with mouse myeloma P3U1.

(2) Cell fusion

P3U1 was cultured in the culture medium A beforehand. Its cell concentration at the time of its use was $6 \times 10^5$ cells/ml. The lymphocytes obtained from the tonsil lot proved to be highly productive of anti-*P. aeruginosa* antibody in the preceding (1) and P3U1 were washed twice respectively with serum-free RPMI 1640. The lymphocytes and $5 \times 10^6$ cells of P3U1 were put into the same test tube, centrifuged at 1500 rpm, and the supernatant was discarded. The cell pellets were dispersed thoroughly by tapping the test tube. The cells were made to suspend gently by adding 0.5 ml of polyethylene glycol liquid (5.75 ml of RPMI 1640+3.5 ml of polyethylene glycol+0.75 ml of dimethyl sulfoxide) (hereinafter abbreviated to PEG liquid). One minute later 0.5 ml of RPMI 1640, another 1 minute later 1 ml of RPMI 1640, another 2 minutes later 4 ml of HAT culture medium (RPMI 1640+2% bovine fetus serum+80 μg/ml gentamicin+95 μM hypoxanthine+0.4 μM aminopterin+1.6 μM thymidine), and another 2 minutes later 4 ml of HAT culture medium were added thereto. Finally a total of 25 ml of cell suspension was prepared by adding HAT culture medium. This was placed in a 96-well culture plate and the culture was continued at 37° C. in the atmosphere containing 5% CO. A half of the culture medium was replaced with new HT culture medium (HAT excepting A) once in every week to obtain hybridomas.

(3) Cloning and culture

The supernatant of the obtained hybridoma was subjected to ELISA with the use of a plate coated with formalin-killed *P. aeruginosa* IFO 3080 and human monoclonal antibody 313 which bound to *P. aeruginosa* IFO 3080 was obtained. Then the 313-producing hybridomas were cloned twice by limiting dilution (2 pieces of 96-well plates) and finally obtained mouse-human hybridomas 313-6 which produce human monoclonal anti-bodies (IgG, γ)

Thus obtained hybridomas were cultured in 1 l of serum-free culture medium RDF/TES serum-free culture medium. The culture broth which contained human monoclonal antibodies was concentrated to 30 ml by use of ultrafiltration membrane PM-30 (Amicon Corp.). The concentrate was subjected to affinity chromatography on Protein A-Sepharose to obtain 15 mg of purified human monoclonal antibodies.

(4) Binding spectrum

The binding spectrum of this human antibody to various strains of *P. aeruginosa* was determined by ELISA. The result is shown in Table 6.

(5) Infection preventive effect of monoclonal antibody

*P. aeruginosa* IFO 3080 and O-32 were chosen to evaluate the protective activity of human monoclonal antibody 313-6 against infection. The serotype of IFO 3080 was M and that of O-32 was F.

Four week ICR mice (male, weighing 16 to 20 g, in groups of 10 mice) were injected intraperitoneally with 10 μg or 1 μg of monoclonal antibodies 313-6. One hour after the injection, IFO 3080 strain or O-32 strain in an amount approximately equal to the minimum lethal dose was intraperitoneally given to the mice. IgG prepared from human serum was injected intraperitoneally as the positive control and the same dose of saline was injected likewise as the negative control. The result of the 5-day observation is shown in Table 7.

TABLE 6

| P. aeroginosa strain | Serotype | ELISA O.D. reading score antibody 313-6 | antibody PEI2G4 | antibody PCR2-1 |
|---|---|---|---|---|
| O-34 | A | 1.0 | 0.5 | 0.2 |
| C-8 | A | 0.9 | 0.5 | 0.2 |
| 122 | A | 0.8 | 0.6 | 0.3 |
| N-1 | A | 1.0 | 1.0 | 0.3 |
| PAO1 | B | 1.0 | 0.5 | 0.3 |
| 97 | B | 0 | 0 | 0 |
| IFO3445 | B | 0.5 | 0.2 | 0.3 |
| 1120 | B | 0.7 | 0.4 | 0.3 |
| C-19 | B | 0 | 0 | 0 |
| 1130 | B | 0.8 | 0.3 | 0.2 |
| IT3 | B | 0 | 0 | 0 |
| IT7 | B | 0.1 | 0 | 0.2 |
| N-3 | C | 0.8 | 0.2 | 0.3 |
| N-26 | C | 0.8 | 0.3 | 0.3 |
| 142 | C | 0.7 | 0.6 | 0.3 |
| N-20 | C | 0.9 | 0.7 | 0.4 |
| IT6 | C | 0.3 | 0 | 0.2 |
| O-101 | E | 0.6 | 0.2 | 0.3 |
| C-12 | E | 0.9 | 0.2 | 0.3 |
| 1237 | E | 0 | 0 | 0 |
| O-56 | E | 0.7 | 0.2 | 0.3 |
| 1227 | E | 0 | 0 | 0 |
| N-2 | E | 0.5 | 0.2 | 0.2 |
| IT2 | E | 1.0 | 0.4 | 0.3 |
| O-102 | F | 0.3 | 0 | 0.1 |
| 1128 | F | 0 | 0 | 0.2 |
| 146 | F | 0.8 | 0.4 | 0.3 |
| 28 | F | 0.8 | 0.6 | 0.4 |
| 64 | F | 1.0 | 1.0 | 0.3 |
| O-32 | F | 1.0 | 1.0 | 0.4 |
| 5 | G | 1.0 | 0.4 | 0.2 |
| O-7 | G | 1.0 | 1.0 | 0.3 |
| O-19 | G | 1.0 | 1.0 | 0.4 |
| IT1 | G | 1.0 | 0.4 | 0.2 |
| O-38 | G | 0.2 | 0.1 | 0.2 |
| O-36 | G | 0.4 | 0.1 | 0.3 |
| O-31 | G | 0.2 | 0.1 | 0.3 |
| 1133 | H | 0.8 | 0.3 | 0.3 |
| O-64 | H | 1.0 | 0.8 | 0.3 |
| O-22 | H | 1.0 | 0.6 | 0.2 |
| 1258 | H | 0.8 | 0.5 | 0.3 |
| IT5 | H | 0.1 | 0 | 0.1 |
| O-25 | I | 0.9 | 0.4 | 0.3 |
| 38 | I | 1.0 | 0.6 | 0.2 |
| O-50 | I | 0.8 | 0.5 | 0.3 |

TABLE 6-continued

| P. aeroginosa strain | Serotype | ELISA O.D. reading score | | |
|---|---|---|---|---|
| | | antibody 313-6 | antibody PEI2G4 | antibody PCR2-1 |
| 1263 | I | 0.9 | 0.7 | 0.3 |
| IT4 | I | 0.3 | 0.1 | 0.2 |
| IFO3080 | M | 1.0 | 1.0 | 0.4 |

TABLE 7

| Dose | number of survivors/ number of tests | |
|---|---|---|
| | IFO 3080 | O-32 |
| 10 μg/mouse | 10/10 | 8/10 |
| 1 μg/mouse | 4/10 | 1/10 |
| 2 μg of human IgG/mouse | 8/10 | 5/10 |
| Saline | 0/10 | 0/10 |

EXAMPLE 10

Selection of antibody producing cells and cell fusion were conducted according to the same way as Example 9. The supernatant of hybridomas thus obtained was subjected to ELISA with use of plates coated with formalin-killed *P. aeruginosa* to obtain human monoclonal antibody PEI2G which strongly binds to *P. aeruginosa* IFO 3080 strain. The hybridomas productive of PEI2G were cloned two times by limiting dilution to obtain mouse-human hybridomas which produce human monoclonal antibodies (IgG) called PEI2G4. The culture supernatant of the hybridomas was subjected to ELISA to study the binding to various *P. aeruginosa* cells. The result is shown in Table 6. As seen clearly from Table 6, the binding mode accorded with that of antibody 313-6.

EXAMPLE 11

Selection of antibody producing cells and cell fusion were carried out by use of human tonsil cells according to Example 9. The obtained hybridoma culture supernatant was subjected to ELISA with use of plates coated with formalin-killed *P. aeruginosa* to obtain antibody PCR2 which bind to *P. aeruginosa* IFO 3080 strain. The hybridomas which produce human monoclonal antibodies were cloned twice by limiting dilution and soft agar method to give hybridomas which produce PCR2-1 (IgM).

The hybridomas were cultured according to the same method as Example 9, partially purified, and subjected to ELISA to study the binding to *P. aeruginosa*. The result is shown in Table 6.

EXAMPLE 12

Binding inhibition test was made to show that the antigen which recognizes human monoclonal antibody 313-6 is E87Ag antigen.

Figure 6:
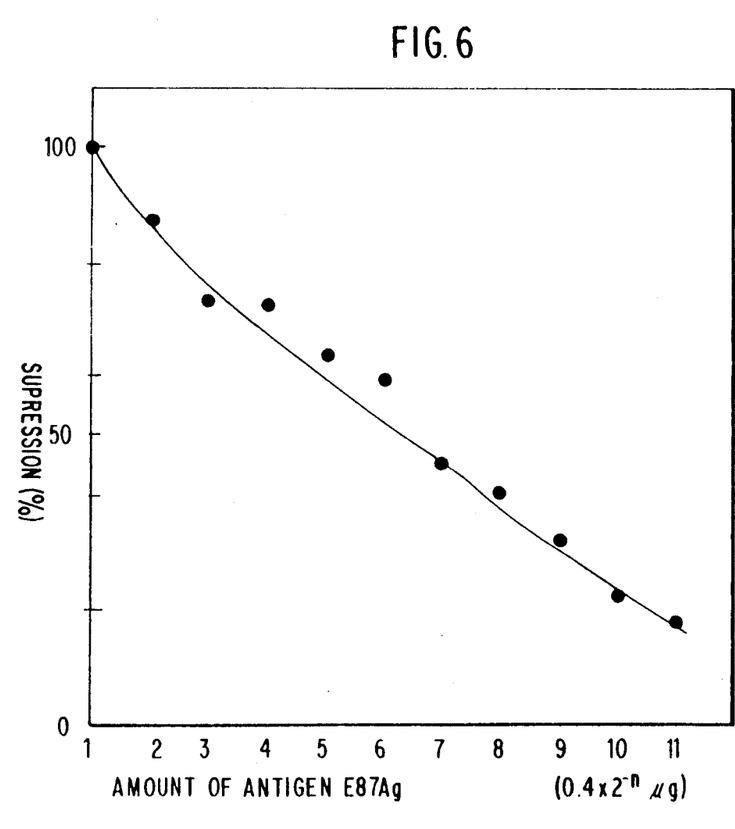
FIG. 6 is a drawing which shows the binding inhibition of human monoclonal antibody 313-6 by E87Ag antigen.

After 0.5 μg of human monoclonal antibody 313-6 was made to react with purified E87Ag antigen for 60 minutes beforehand, the reaction mixture was subjected to ELISA to determine the binding of antibody 313-6 to IFO 3080. The result is shown in FIG. 6. As shown in FIG. 6, the ELISA binding activity of 313-6 was inhibited by E87Ag antigen corresponding to the concentration, leading to the confirmation that antibody 313-6 recognized E87Ag antigen.

EXAMPLE 13

The agglutination activity of antibody 313-6 was tested with the use of various strains of *P. aeruginosa*. Each well of a 96-well U plate was filled with 50 μl of antibody 313-6 (20 μg/ml) and 5 μl of formalin-killed *P. aeruginosa* ($1 \times 10^{10}$/ml) was added. After the plate was left standing overnight at room temperature, the observation was made with the naked eye. The result is shown in Table 8.

TABLE 8

| Agglutinable P. aeruginosa | Not agglutinable P. aeruginosa |
|---|---|
| N-1, 64, O-32, O-7, O-19, O-64, 1263, IFO 3080 | O-34, C8, 122, PAO-1, 97, IFO 3445, 1120, C-19, 1130, IT3, IT7, N-3, N-26, 142, N-20, IT6, IT2, O101, C-12, 1237, O-56, 1127, N-2, O-102, 1128, 146, 28, 5, IT1, O-38, O-36, 1133, O-22, 1258, IT-5, O-31, O-25, 38, O-50, IT-4 |

EXAMPLE 14

The binding an agglutination activity of antibody 313-6 to strains of *P. aeruginosa* clinically isolated from patients with cystic fibrosis and DPB was studied. The result of the study is shown in Table 9.

TABLE 9

| | Clinically isolated strain | Serotype | ELISA score | Agglutination activity |
|---|---|---|---|---|
| Cystic birosis | F 1619 | F | 0.6 | — |
| | F 1769 | I | 1.0 | — |
| | F 1769-1 | I | 0.9 | — |
| | F 1753-1 | nontypable | 1.0 | + |
| | F 1753-2 | " | 0.9 | + |
| | F 1881 | A | 0.5 | — |
| | F 1950-1 | nontypable | 0.9 | + |
| | F 1950-2 | " | 1.0 | + |
| | F 1950-3 | " | 0.7 | + |
| | F 1998 | " | 0.9 | + |
| DPB | YS | nontypable | 0 | — |
| | AZ | " | 0.8 | + |
| | FZ | " | (not measured) | + |
| | TR | H | (not measured) | — |

As apparent from Table 9, antibody 313-6 showed a tendency to agglutinate the strains, whose serotype were nontypable, among the cystic fibrosis strain and DPB strain.

EXAMPLE 15

The agglutination activity of antibody 313-6 to *P. aeruginosa* strains whose serotypes were nontypable was also studied. The result is shown in Table 10.

TABLE 10

| P. aeruginosa strain | Agglutination activity |
|---|---|
| O-2 | + |
| O-9 | + |
| Tid29 | — |
| Tid38 | + |
| O-47 | — |
| Tid53 | + |
| O-67 | + |
| O-68 | + |
| 110 | + |
| 117 | + |
| 118 | + |
| 1121 | + |

TABLE 10-continued

| P. aeruginosa strain | Agglutination activity |
|---|---|
| 1126 | + |

As seen from Table 10, antibody 313-6 agglutinated most of the strains whose serotypes were nontypable.

EXAMPLE 16

ICR mice (4-week old, male) were intraperitoneally injected with 10 μg or 1 μg of antibody 313-6 and one hour later they were intraperitoneally administered with $2LD_{50}$ ($3 \times 10^7$) of cystic fibrosis isolated strain F1998. IgG prepared from human serum was injected intraperitoneally as the positive control and the same amount of saline was likewise given as the negative control. The result of 5-day observation is shown in Table 11.

TABLE 11

| Dose | Number of survivors/ number of tests |
|---|---|
| 10 μg/mouse | 10/10 |
| 1 μg/mouse | 7/10 |
| 2 mg of human IgG/mouse | 5/10 |
| Saline | 0/10 |

INDUSTRIAL APPLICATIONS

Antigen E87Ag of this invention bind to P. aeruginosa mouse monoclonal antibody E87 (IgG2a). Also, it has characteristic properties of not showing any endotoxicity to living bodies and displaying a high degree of immunogenicity. Therefore, antigen E87Ag of this invention can be used as the vaccine for humans and animals such as a mink against P. aeruginosa infections. The preparation of vaccine can be carried out according to common method. For instance, it can be prepared by dissolving antigen E87Ag together with a proper amount of adjuvants such as aluminum hydroxide, aluminum phosphate, calcium phosphate, and alum, in a solvent such as distilled water and saline under the sterile conditions. In case where increased immunogenicity is required, it may be prepared by binding antigen E87Ag to proper protein such as albumin. The dose may be of any amount so far as it is effective enough to induce immune response in the host and it is administered subcutaneously, intramuscularly, or intradermally. The mouse-or human-mouse hybridomas of this invention, which are selected by cloning and productive of anti-P. aeruginosa mouse or human monoclonal antibody E87, can be freeze-stored and also can be mass-cultured by any appropriate method. When the hybridomas are mass-cultured by a proper method, anti-P. aeruginosa monoclonal antibody E87 can be obtained from the culture supernatant. Also, anti-P. aeruginosa monoclonal antibody E87 can be obtained from the ascites and blood serum of animals implanted of this hybridoma. Anti-P. aeruginosa monoclonal antibody E87 is purified by affinity chromatography with the use of monoclonal antibodies.

The monoclonal antibody E87 of this invention can be used as a testing reagent and labelling reagent with remarkable accuracy and reliability in the handling of P. aeruginosa.

The anti-P. aeruginosa human monoclonal antibody which recognize E87Ag binds to P. aeruginosa specifically and cause P. aeruginosa to undergo immune bacteriolysis with its complement. Also it can protect the mice against infection in the model test of challenging mice with P. aeruginosa by agglutinating P. aeruginosa or making P. aeruginosa inclined to be opsonized by leukocytes (opsonic activity). The method of administering human monoclonal antibody which recognized E87Ag various depending upon the individual case including the conditions of P. aeruginosa infectious disease to be treated, amount of the dose, and frequency of administration. It is a general practice to mix the antibody with a nonpoisonous, pharmaceutically permissible carrier such as saline solution prior to its administration and to give such a preparation by a suitable medical method such as intravenous injection, etc. The antibody is usually made to be contained in the carrier at a concentration ranging from 0.5 μg antibody/ml to 500 μg/ml. The amount of antibody per dose is in the range of 10 μg to 10 mg per kg of body weight. As the case may require, it can be administered in a series of more than once.

We claim:

1. The P. aeruginosa E87Ag antigen, wherein said antigen:
   (a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
   (b) has a molecular weight of approximately 27,000 Daltons when measured by a Sephacryl S-300 gel filtration chromatography;
   (c) is a neutral polysaccharide comprised essentially of about 90% by weight of rhamnose without any detectable contamination of protein; and
   (d) preserves its antigenic profile across different serotypes of P. aeruginosa.

2. A monoclonal antibody which binds specifically to the E87Ag antigen, found in the lipopolysaccharide fraction of P. aeruginosa serotype M, wherein said antigen:
   (a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
   (b) has a molecular weight of approximately 27,000 Daltons when measured by a Sephacryl S-300 gel filtration chromatography;
   (c) is a neutral polysaccharide comprised essentially of about 90% by weight of rhamnose without any detectable contamination of protein; and
   (d) preserves it santigenic profile across different serotypes of P. aeruginosa.

3. The anti-P. aeruginosa monoclonal antibody according to claim 2, wherein said antibody is a human monoclonal antibody.

4. The anti-P. aeruginosa monoclonal antibody according to claim 2, wherein said antibody is a mouse monoclonal antibody.

5. A process for producing a monoclonal antibody comprising the steps of:
   (1) preparing hybridomas and/or cell lines arising therefrom, by fusing human cells that produce said anti-P. aeruginosa antibody with mouse myeloma cells;

(2) selecting hybridomas that produces a human monoclonal antibody which specifically binds an E87Ag antigen, found in the lipopolysaccharide fraction of P. aeruginosa serotype M, wherein said antigen:
(a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
(b) has a molecular weight of approximately 27,000 Daltons when measured by a Sephacryl S-300 gel filtration chromatography;
(c) is a neutral polysaccharide comprised essentially of about 90% by weight of rhamnose without any detectable contamination of protein; and
(d) preserves its antigenic profile across different serotypes of P. aeruginosa;
(3) culturing at least one of said hybridomas and/or said cell lines arising therefrom, and
(b 4) collecting said human monoclonal antibody from the culture.

6. A process for producing a mouse monoclonal antibody comprising:
(1) preparing hybridomas by fusing antibody producing cells of mice immunized with P. aeruginosa serotype M that have antigen E87Ag with mouse myeloma cells;
(2) selecting hybridomas and/or cell lines arising therefrom, that produce a human monoclonal antibody which specifically binds an E87Ag antigen, found in the lipopolysaccharide fraction of P. aeruginosa serotype M, wherein said antigen:
(a) is isolated from a polysaccharide fraction having a molecular weight of about 25,000 to 35,000 Daltons said fraction being obtained by hydrolyzing P. aeruginosa lipopolysaccharide with a weak acid, removing lipid A. and subjecting the acid treated polysaccharide void of the lipid A to gel filtration;
(b) has a molecular weight of approximately 27,000 Daltons when measured by a Sephacryl S-300 gel filtration chromatography;
(c) is a neutral polysaccharide comprised essentially of about 90% by weight of rhamnose without any detectable contamination of protein; and
(d) preserves its antigenic profile across different serotypes of P. aeruginosa.
(3) culturing at least one of said hybridomas and/or said cell lines arising therefrom, and
(4) collecting said human monoclonal antibody from the culture.

7. A hybridoma or cell line arising therefrom that produces a human monoclonal antibody which is obtained by fusing mouse myeloma cells with human cells that produce anti-P. aeruginosa antibodies, at least one of said antibody specifically binding an E87Ag antigen, said antigen, found in the lipopolysaccharide fraction of P. aeruginosa serotype M, wherein said antigen:
(a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
(b) has a molecular weight of approximately 27,000 Daltons when measured by a Sephacryl S-300 gel filtration chromatography;
(c) is a neutral polysaccharide comprised essentially of about 90% by weight of rhamnose without any detectable contamination of protein; and
(d) preserves its antigenic profile across different serotypes of P. aeruginosa.

8. A hybridoma or cell line arising therefrom that produces a mouse monoclona antibody which is obtained by fusing mouse myeloma cells with antibody producing cells of mice immunized with P. aeruginosa serotype M that have antigen E87Ag, said mouse monoclonal antibody specifically binding an E87Ag antigen, found in the lipopolysaccharide fraction of P. aeruginosa serotype M, wherein said antigen:
(a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
(b) has a molecular weight of approximately 27,000 Daltons when measured by a Sephacryl S-300 gel filtration chromatography;
(c) is a neutral polysaccharide comprised essentially of about 90% by weight of rhamnose without any detectable contamination of protein; and
(d) preserves its antigenic profile across different serotypes of P. aeruginosa.

9. A therapeutic agent for infections of P. aeruginosa comprising:
(1) a therapeutically effective amount of a human monoclonal antibody which specifically binds an E87Ag antigen, found in the lipopolysaccharide fraction of P. aeruginosa serotype M, wherein said antigen:
(a) is isolated from a polysaccharide fraction having a molecular weight of about 25,000 to 35,000 Daltons said fraction being obtained by hydrolyzing P. aeruginosa lipopolysaccharide with a weak acid, removing lipid A, and subjecting the acid treated polysaccharide void of the lipid A to gel filtration;
(b) has a molecular weight of approximately 27,000 Daltons when measured by a Sephacryl S-300 gel filtration chromatography;
(c) is a neutral polysaccharide comprised essentially of about 90% by weight of rhamnose without any detectable contamination of protein; and
(d) preserves its antigenic profile across different serotypes of P. aeruginosa; and
(2) a pharmaceutically acceptable carrier.

10. A therapeutic agent for infections with P. aeruginosa according to claim 9, wherein infections with P. aeruginosa are caused by P. aeruginosa whose serotypes are nontypable.

* * * * *